US00PP33056P2

(12) United States Plant Patent
O'Connell

(10) Patent No.: US PP33,056 P2
(45) Date of Patent: May 11, 2021

(54) ***ALOE* PLANT NAMED 'ALLIGATOR'**

(50) Latin Name: ***Aloe* hybrid**
Varietal Denomination: ALLIGATOR

(71) Applicant: Altman Specialty Plants, Inc, Vista, CA (US)

(72) Inventor: Renee O'Connell, Escondido, CA (US)

(73) Assignee: altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 16/873,317

(22) Filed: Mar. 17, 2020

(51) Int. Cl.
*A01H 5/12* (2018.01)
*A01H 6/00* (2018.01)

(52) U.S. Cl.
USPC ..... Plt./373
CPC ..... *A01H 6/00* (2018.05)

(58) Field of Classification Search
USPC ..... Plt./373
CPC ..... A01H 5/12; A01H 5/02; A01H 5/00
See application file for complete search history.

*Primary Examiner* — Kent L Bell
(74) *Attorney, Agent, or Firm* — Cassandra Bright

(57) ABSTRACT

A new and distinct cultivar of *Aloe* plant named 'ALLIGATOR' is disclosed, characterized by upright rosette of rigid green leaves, liberally dappled with light yellow-green or greyed-green spots and margined by reddish teeth, colored near Greyed-Red 180A. Plants tolerate full sun as well as observed low temperature tolerance to −2° C. Offsets form freely on plants with maturity, creating ornate clusters. The new variety is an *Aloe*, typically produced as a garden or container plant.

1 Drawing Sheet

Latin name of the genus and species: *Aloe* hybrid.
Variety denomination: 'ALLIGATOR'.

BACKGROUND OF THE INVENTION

The new cultivar is a product of a planned breeding program. The seed parent is the unpatented proprietary *Aloe* hybrid 'FRK 02'. The pollen parent is the unpatented proprietary *Aloe* hybrid 'FRK 17'. The crossing was made in March 2014 at a commercial greenhouse in Vista, Calif. 'ALLIGATOR' was selected by the inventor in September 2015.

Asexual reproduction of the new cultivar 'ALLIGATOR' was first performed by tissue culture at a commercial laboratory in Vista, Calif. in October 2015. 'ALLIGATOR' has since produced several generations and has shown that the unique features of this cultivar are stable and reproduced true to type.

SUMMARY OF THE INVENTION

The cultivar 'ALLIGATOR' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'ALLIGATOR'. These characteristics in combination distinguish 'ALLIGATOR' as a new and distinct *Aloe* cultivar:

1. *Aloe* 'Alligator' forms an attractive, upright rosette of rigid green leaves, liberally dappled with light yellow-green or greyed-green spots and margined by reddish teeth, colored near Greyed-Red 180A.
2. *Aloe* 'Alligator' has demonstrated its value as a landscape plant that can be produced in full sun.

3. *Aloe* 'Alligator' has exhibited cold tolerance to −2° C. with no disfiguring.
4. *Aloe* 'Alligator' produces offsets at larger pot size such as an 8" or 10", creating an ornate cluster.

PARENTAL COMPARISON

Plants of the new cultivar 'ALLIGATOR' are similar to the seed parent in most horticultural characteristics. However, plants of the new variety differ from the seed parent in the following:

1. *Aloe* 'Alligator' grows to a larger diameter than does *Aloe* 'FRK 02'.
2. *Aloe* 'Alligator' does not exhibit the more upturned morphology of the leaves that *Aloe* 'FRK 02' displays.
3. *Aloe* 'Alligator' exhibits stronger marginal teeth than does *Aloe* 'FRK 02'.
4. *Aloe* 'Alligator' produces more offsets than does *Aloe* 'FRK 02', and retains a more ornate morphology.

Plants of the new cultivar 'ALLIGATOR' are similar to the pollen parent in most horticultural characteristics. However, plants of the new variety differ in the following:

1. *Aloe* 'Alligator' produces offsets, whereas as *Aloe* 'FRK 17' remains solitary.
2. *Aloe* 'Alligator' exhibits a larger diameter to the rosette than does *Aloe* 'FRK 17'.
3. *Aloe* 'Alligator' has more dappled light yellow-green or greyed-green spots than does *Aloe* 'FRK 17'.

COMMERCIAL COMPARISON

'ALLIGATOR' can be compared to the unpatented commercial variety *Aloe* 'Blue Elf'. The two *Aloe* varieties are similar in most horticultural characteristics; however, the new variety differs in the following:

1. *Aloe* 'Alligator' produces ornate rosettes of rigid green leaves, liberally dappled with light yellow-green or greyed-green spots, whereas *Aloe* 'Blue Elf' exhibits taller rosettes of longer matte blue leaves with no spots.
2. *Aloe* 'Alligator' fills an 8" pot with a single cut, whereas *Aloe* 'Blue Elf' fills an 8" pot only after a much longer interval with the production of offsets.
3. *Aloe* 'Alligator' displays wide, strong leaves which are contained within the perimeter of the pot, whereas *Aloe* 'Blue Elf' produces softer, longer leaves which can break in shipping.
4. *Aloe* 'Alligator' forms thick, rigid leaves that do not "blanch" or exhibit "tip death", whereas those of *Aloe* 'Blue Elf' are thinner and are known to suffer "blanch" or "tip death" under certain circumstances in the commercial environment.

BRIEF DESCRIPTION OF THE PHOTOGRAPH

The accompanying photograph illustrates in full color a top view of a typical plant of 'ALLIGATOR' grown in a greenhouse in Vista, Calif. This plant is approximately 10 months old, shown in a 6-inch container. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart, 2007 edition, except where general terms of ordinary dictionary significance are used. The following observations and measurements describe 'ALLIGATOR' plants in a commercial greenhouse in Vista, Calif. Temperatures ranged from 21° C. to 25° C. during the day, and 18° C. to 21° C. during the night. No artificial light, photoperiodic treatments or chemical treatments were given to the plants. Natural light conditions were approximately 2500 to 3000 fc of light. Measurements and numerical values represent averages of typical plant types.

Botanical classification: *Aloe* hybrid 'ALLIGATOR'.

Age of the plant described: About 1 year.

PROPAGATION

Time to initiate roots: Approximately 25 days at 22° C.

Root description: Fibrous. Brown, not accurately measured with The R.H.S. Chart.

Propagation method: Tissue culture.

PLANT

Growth habit: Single rosette, offsetting freely with maturity.

Container size: 10 inch.

Height: Approximately 17 cm to top of highest leaf. Approximately 75 cm to top of inflorescence.

Plant spread: Approximately 27 cm.

Growth rate: Moderate.

Branching characteristics: No branches, rosette forming.

FOLIAGE

Leaf:

- *Arrangement*.—Rosette.
- *Average length*.—Average range 12-14 cm.
- *Average width*.—5 cm.
- *Average thickness*.—About 15 to 20 mm at thickest.
- *Shape of blade*.—Deltoid.
- *Apex*.—Acute, with a sharp dentation.
- *Base*.—Clasping.
- *Margin*.—Sharp dentations occurring at regular intervals of 5 to 7 mm.
- *Texture of top surface*.—Smooth.
- *Texture of bottom surface*.—Smooth.
- *Quantity of leaves*.—Average range of about 24 to 29 on a 2-year old plant.
- *Color*.—Young foliage upper side: Near RHS Green 137A with linear speckles near Yellow-Green 147D. Speckles about 2 to 3 mm wide and 4 to 7 mm long. Marginal dentations flushed Greyed-Red 180A. Young foliage under side: Near RHS Green 137A with linear speckles near Yellow-Green 147D. Speckles about 2 to 3 mm wide and 4 to 7 mm long. Marginal dentations flushed Greyed-Red 180A. Mature foliage upper side: Near RHS Green 137A with linear speckles near Greyed-Green193B. Speckles about 2 to 3 mm wide and 4 to 7 mm long. Marginal dentations flushed Greyed-Red 180A. Mature foliage under side: Near RHS Green 137A with linear speckles near Greyed-Green193B. Speckles about 2 to 3 mm wide and 4 to 7 mm long. Marginal dentations flushed Greyed-Red 180A.
- *Venation*.—Linear. Color: Indistinguishable from leaf blade.

FLOWER

Natural flowering season: Late Fall to early Winter in Southern California.

Inflorescence type and habit: Raceme.

Flower longevity on plant: About 1.5 months.

Quantity of flowers: 30 to 40 on average.

Total inflorescence size:

- *Height*.—Approximately 30 cm.
- *Width*.—Approximately 7.5 cm.

Flower bud:

- *Shape*.—Cylindrical.
- *Length*.—Approximately 1.5 cm.
- *Diameter*.—Approximately 5 mm.
- *Color*.—Near RHS Yellow-Green 144B, base near Orange-Red 31A.

Corolla:

- *Arrangement*.—Tubular, opening slightly at apex with age.
- *Length*.—Approximately 3.0 to 3.5 cm.
- *Width*.—Approximately 1.4 cm at widest point.
- *Color*.—Immature: Outer Surface: Near RHS Orange-Red 32B, apex near Yellow-Green 144C. Inner Surface: RHS Orange 29C, apex near Yellow-Green 144C. Mature: Outer Surface: Near RHS Orange-Red 43B, flushed 28C, upper ⅓ streaked Yellow-Green 144A. Inner Surface: RHS Orange 29D, apex near Yellow-Green 144C.

Calyx: Absent.

Fragrance: None.

Pedicel:

- *Length*.—Approximately 1.1 cm.
- *Width*.—2 mm.
- *Aspect*.—Upright.
- *Color*.—Near RHS Yellow-Green 146B when immature, near Greyed-Orange 177B at maturity.
- *Texture*.—Glabrous.

Peduncle:

- *Length*.—Approximately 40 to 45 cm.
- *Width*.—6-8 mm.
- *Aspect*.—Upright when immature, dropping slightly at maturity.

*Color*.—Near RHS Yellow-Green 146B.
*Texture*.—Glabrous.

REPRODUCTIVE ORGANS

Stamens:
*Number*.—6.
*Filament length*.—2.5 cm.
*Filament color*.—RHS Green-Yellow 1B.
*Anther length*.—About 3 mm.
*Anther color*.—RHS Orange-Red 32A.
*Anther shape*.—Oval.
*Pollen color*.—RHS Orange-Red 33A.
*Pollen quantity*.—Moderate.
Pistil:
*Number*.—1.
*Length*.—Approximately 2.7 cm.
*Style color*.—RHS Yellow 2B.
*Stigma*.—Shape: Linear. Color: RHS Yellow 2B. Ovary color: RHS Yellow-Green 144A.

OTHER CHARACTERISTICS

Seeds and fruits: Not observed to date. Seed pods not observed to form.
Temperature tolerance: Tolerates temperatures from approximately 28° C. to −2° C.
Disease/pest resistance: Neither resistance nor susceptibility observed.

What is claimed is:

1. A new and distinct cultivar of *Aloe* plant named 'ALLIGATOR' as herein illustrated and described.

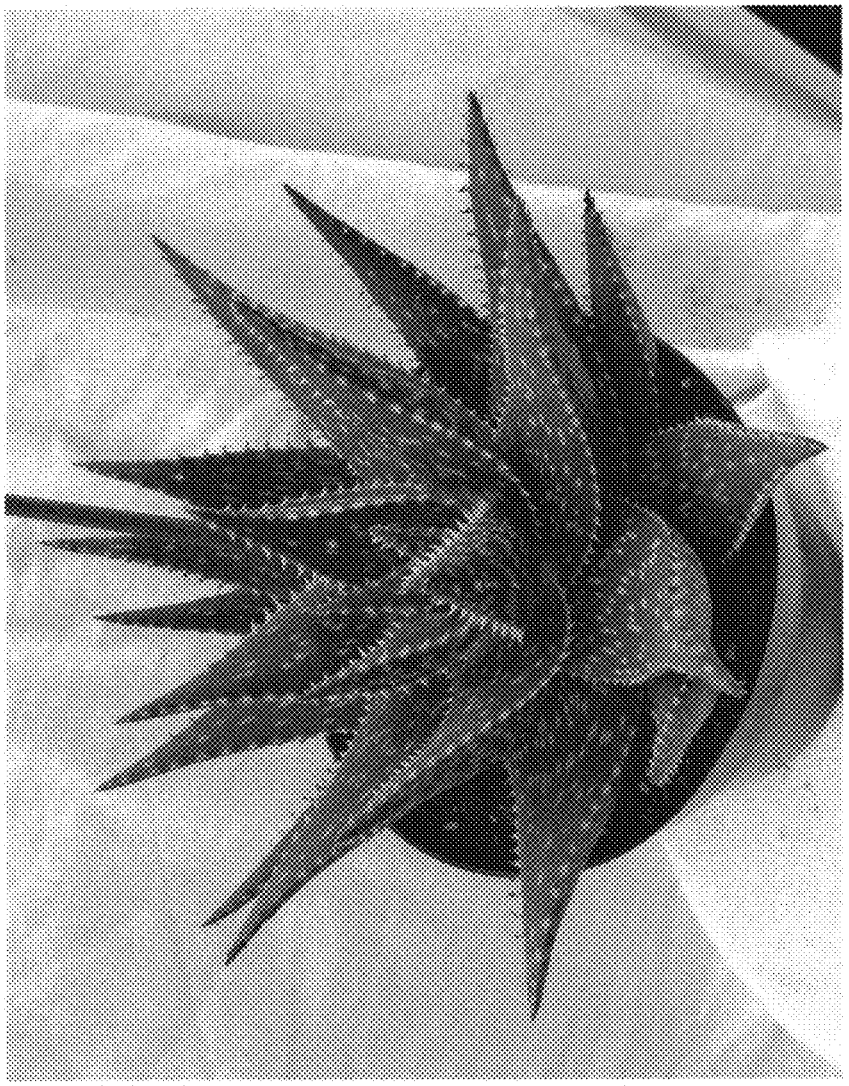

* * * * *